United States Patent [19]

Chikama

[11] Patent Number: 5,002,041
[45] Date of Patent: Mar. 26, 1991

[54] BENDING DEVICE AND FLEXIBLE TUBE STRUCTURE

[75] Inventor: Toshio Chikama, Tokyo, Japan

[73] Assignee: Kabushiki Kaisha Machida Seisakusho, Tokyo, Japan

[21] Appl. No.: 519,593

[22] Filed: May 7, 1990

[30] Foreign Application Priority Data

| May 12, 1989 | [JP] | Japan | 1-117451 |
| Aug. 22, 1989 | [JP] | Japan | 1-214223 |
| Mar. 14, 1990 | [JP] | Japan | 2-61202 |

[51] Int. Cl.⁵ ............................................. A61B 1/00
[52] U.S. Cl. .................................................. 128/4
[58] Field of Search ................................ 128/4, 6, 778

[56] References Cited

U.S. PATENT DOCUMENTS

| 3,739,770 | 6/1973 | Mori | 128/6 |
| 3,749,086 | 7/1973 | Kline et al. | |
| 4,329,980 | 5/1982 | Terada | 128/4 |
| 4,432,349 | 2/1984 | Oshiro | 128/4 |
| 4,690,175 | 9/1987 | Ouchi et al. | 128/4 X |
| 4,805,596 | 2/1989 | Hatori | 128/4 |

FOREIGN PATENT DOCUMENTS

| 259945 | 3/1988 | European Pat. Off. |
| 48-31669 | 9/1973 | Japan |
| 529274 | 2/1977 | Japan |
| 55-10605 | 1/1980 | Japan |
| 57-130602 | 8/1982 | Japan |
| 5936 | 1/1984 | Japan |
| 62-18102 | 2/1987 | Japan |

Primary Examiner—William H. Grieb
Attorney, Agent, or Firm—Fish & Richardson

[57] ABSTRACT

A flexible tube structure includes a coil assembly including a plurality of coils which are combined together in such a manner that turns of the plurality of coils alternate with each other. Any two adjacent turns of the plurality of coils are disposed in substantially point-to-point contact relation to each other. There is also disclosed a bending device in which an operating wire is passed through at least one axially-extending space formed between peripheries of the plurality of coils. A distal end of the operating wire is fixed relative to a distal end of the coil assembly.

14 Claims, 7 Drawing Sheets

BENDING DEVICE AND FLEXIBLE TUBE STRUCTURE

BACKGROUND OF THE INVENTION

This invention relates to a bending device and a flexible tube structure which are used, for example, in an endoscope.

As is well known, an endoscope comprises a hollow body, a flexible insertion portion extending from a front end of the body, a flexible bending portion extending from a distal end of the insertion portion, and a rigid portion formed on a distal end of the bending portion.

In conventional bending portions (bending devices) for an endoscope as disclosed in Japanese Utility Model Publication No. 31669/73 and Japanese Laid-Open (Kokai) Utility Model Application No. 130602/82, a number of tubular elements are arranged axially. Each tubular element has axially-extending connective portions, and the connective portions of the adjacent tubular elements are connected together by riveting, thereby interconnecting the adjacent tubular elements in a manner to allow a relative angular movement therebetween. A guide portion is formed on the inner peripheral surface of each tubular element, or a guide member is fixedly secured to the inner peripheral surface of each tubular element. An operating wire is guided by such guide means. The proximal end of the operating wire is connected to an manipulating member mounted on the above body whereas the distal end is fixedly secured to the rigid portion. The manipulating member is operated to pull the operating wire, so that the bending portion is bent or curved so as to direct the rigid portion in a desired direction. The bending portion has an axially-extending internal space, and a bundle of optical fibers for transmitting illumination light, a bundle of optical fibers for transmitting an image, and a guide tube for guiding a forceps are passed through this internal space.

In the bending portion of the above construction, much time and labor are required for the working or processing of the tubular elements and for pressing rivets. This results in an increased manufacturing cost of the bending portion. Particularly when manufacturing the bending portion of a narrow construction, the manufacturing cost has been very high. Further, since the guide portion or the guide member for guiding the operating wire is projected from the inner peripheral surface of the tubular element, there is a possibility that the optical fiber bundles, etc., inserted in the internal space may be damaged by the guide portion or the guide member when the bending portion is bent.

A conventional insertion portion (flexible tube structure) for an endoscope, as disclosed in Japanese Laid-Open Patent Application No. 36/84, comprises a holder coil formed by winding a strip-like plate, a braid tube formed around the outer periphery of the holder coil, and an outer sheath of a resin covering the braid tube. Any two adjacent turns of the holder coil are spaced apart from each other.

The insertion portion of the above construction is excellent in flexibility, but has a drawback that it contracts axially. This drawback arises from the facts that the braid tube hardly offers a resistance to a compressive force tending to axially contract the insertion portion, and that the holder coil and the outer sheath are resilient in the axial direction. Therefore, particularly when the insertion portion is of the narrow type so as to be inserted into the trachea or the blood vessel, the insertion portion is axially contracted due to resistances offered by the trachea or the blood vessel, and can not be smoothly inserted thereinto.

With respect to another prior art flexible tube structure, Japanese Laid-Open Utility Model Application No. 18102/87 discloses a guide tube for guiding a forceps in an endoscope. This guide tube comprises one coil, and a resilient resin tube.

SUMMARY OF THE INVENTION

It is a first object of this invention to provide a bending device which can be manufactured at much less costs.

A second object of this invention is to provide a flexible tube structure which will not contract axially.

In order to achieve the first object, according to one aspect of the present invention, there is provided a bending device comprises:

(a) operating wire means adapted to be pulled at a proximal end thereof; and (b) a coil assembly comprising a plurality of coils which are combined together in such a manner that turns of the plurality of coils alternate with each other, any two adjacent turns of the plurality of coils being disposed in substantially point-to-point contact relation to each other, space means extending axially of the coils and being formed between peripheries of the plurality of coils, the operating wire means being passed through the space means, and a distal end of the operating wire means being substantially fixed relative to a distal end of the coil assembly.

In order to achieve the second object, according to another aspect of the present invention, there is provided a flexible tube structure comprising:

(a) flexible outer tube means; and (b) a coil assembly mounted within the outer tube means, the coil assembly comprising a plurality of coils which are combined together in such a manner that turns of the plurality of coils alternate with each other, any two adjacent turns of the plurality of coils being disposed in substantially point-to-point contact relation to each other, and an internal space being formed by an inner periphery of at least one of the plurality of coils.

DESCRIPTION OF THE PREFERRED EMBODIMENTS OF THE INVENTION

The invention will now be described with reference to the drawings.

Figure 1:
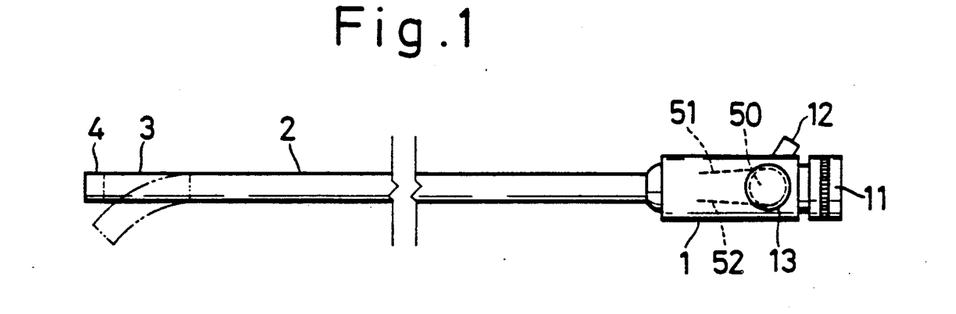
FIG. 1 is a schematic view of an endoscope.

An endoscope shown in FIG. 1 comprises a hollow body 1, an insertion portion 2 extending from a front end of the body 1, a bending portion 3 extending from a distal end of the insertion portion 2, and a rigid portion 4 mounted on a distal end of the bending portion 3. The insertion portion 2 as well as the bending portion 3 has a cylindrical shape, and is flexible so as to be bent.

An ocular tube 11 is mounted on the rear end of the body 1, and a forceps insertion inlet 12 for introducing an elongated forceps, as well as a manipulation dial 13, is provided on the side of the body 1. A cable (not shown) is fixedly connected at one end to the side of the body 1, and a connector connectable to a light source is mounted on the other end of this cable.

Figure 2:
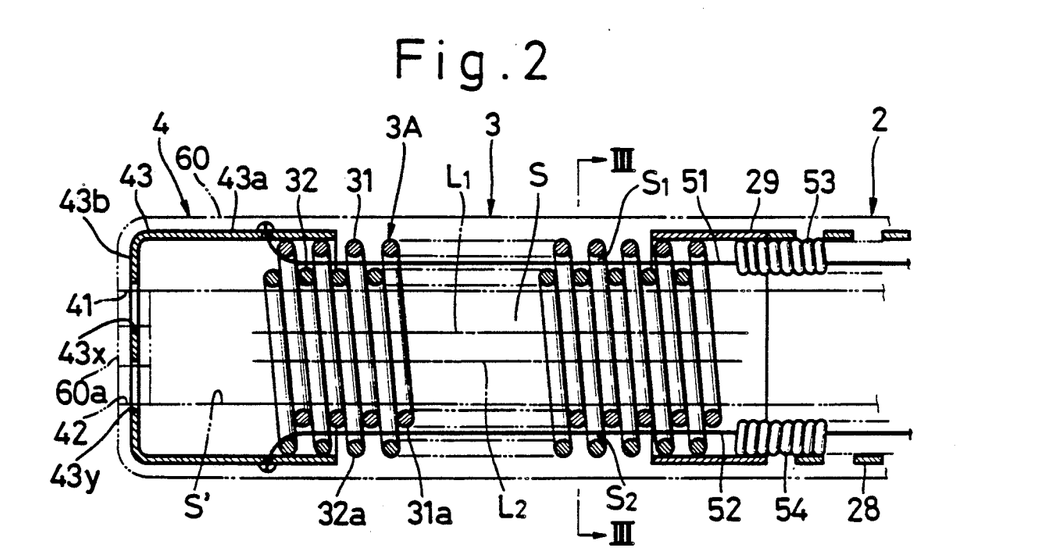
FIG. 2 is an enlarged, cross-sectional view of an important portion of the endoscope, showing a bending portion thereof.

As shown in FIG. 2, an inspection window 41, an illumination window 42, a forceps outlet (not shown) and etc., are provided at the rigid portion 4. The ocular portion 11 is connected to the inspection window 41 via an imagetransmitting optical system (not shown) passing through the body 1, the insertion portion 2 and the bending portion 3, this optical system including a bundle of optical fibers. With this arrangement, an observation can be done through the ocular portion 11. Illumination light from the light source is supplied to the illumination window 42 via a bundle of optical fibers passing through the connector, the cable, the body 1, the insertion portion 2 and the bending portion 3. The forceps outlet is connected to the forceps insertion inlet 12 via a guide tube (not shown) extending through the bending portion 3, the insertion portion 2 and the body 1.

As shown in FIG. 2, the insertion portion 2 includes a holder coil 28 composed of a strip-like plate. A proximal end of the holder coil 28 is fixedly secured to the body 1, and a connecting tube 29 is fixedly secured to the distal end of the holder coil 28.

The rigid portion 4 includes a frame 43 which has a tubular portion 43a and an end wall 43b formed at the distal end of the tubular portion 43a. A plurality of holes 43x, 43y ... are formed through the end walls 43b, and are disposed in registry with the inspection window 41, the illumination window 42, etc., respectively.

Figure 3:
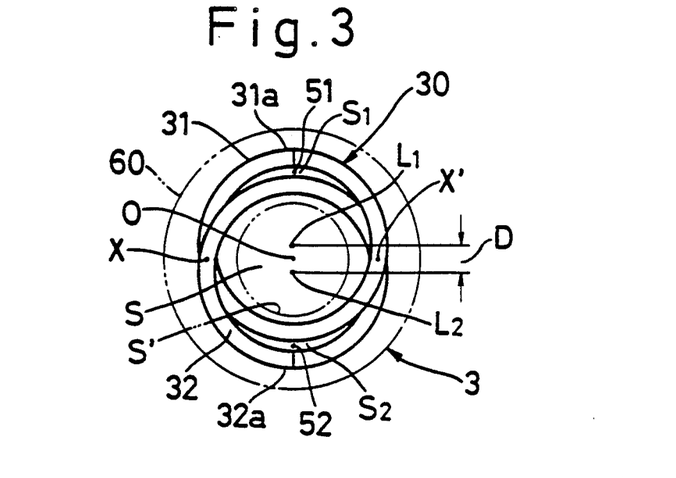
FIG. 3 is a cross-sectional view taken along the line III—III of FIG. 2, a transverse cross-section of each coil being indicated by a line for illustration purposes.

The bending portion 3 comprises a coil assembly 30 composed of two coils 31 and 32. The two coils 31 and 32 are of an identical shape, and are substantially circular as viewed in the direction of the axis thereof, as shown in FIG. 3.

One example of a method of assembling the coil assembly 30 will now be described One coil 31 is fitted on an outer periphery of a core member of a circular cross-section, and in this condition the other coil 32 is threaded (that is, rotated about its axis and is axially moved) relative to the one coil 31 until the opposite ends of the other coil 32 are brought into registry with the opposite ends of the one coil 31, respectively. Then, the thus connected coils 31 and 32 are removed from the core member, and then the two coils 31 and 32 are displaced with respect to each other in such a manner that their axes L1 and L2 are radially spaced apart from each other.

The coil assembly 30 can be assembled by another method. In this method, the two coils 31 and 32 are first disposed in substantially parallel spaced, opposed relation to each other, and the two coils 31 and 32 are radially moved relative to each other to be coupled to each other. In this case, preferably, the two coils 31 and 32 are axially expanded, and in this condition they are radially moved relative to each other to be coupled together, and then the axial expansion of each coil is released In this method, the direction of turn or winding of the coil 31 may be different from that of the coil 32.

The construction of the coil assembly 30 will now be described in further detail. The axes L1 and L2 of the coils 31 and 32 are parallel to each other and are spaced from each other a distance D slightly greater than the diameter (thickness) of each of wires 31a and 32a respectively constituting the coils 31 and 32. Therefore, the coils 31 and 32 are disposed symmetrically with respect to a center line 0 of the coil assembly 30 disposed centrally of the distance D between the axes L1 and L2. The turns of the coils 31 and 32 alternate with each other. The pitch of each of the coils 31 and 32 is twice greater than the diameter or thickness of each of the wires 31a and 32a of a circular cross-section. Any two adjacent turns of the coils 31 and 32 are disposed in contact with each other at two points X and X'. The two contact points X and X' lie respectively on two straight lines parallel to the center line 0. These two straight lines are disposed in a plane (passing through the center line 0) perpendicular to a plane which passes through the axes L1 and L2 of the coils 31 and 32.

An axially-extending space S1 is formed between the inner periphery of the coil 31 and the outer periphery of the coil 32, and similarly an axially-extending space S2 is formed between the outer periphery of the coil 31 and the inner periphery of the coil 32. An internal space S is formed by the inner peripheries of the two coils 31 and 32.

The proximal end portions of the coils 31 and 32 of the coil assembly 30 are fixed to the inner peripheral surface of the connecting tube 29. The distal end portions of the coils 31 and 32 are fixed to the inner peripheral surface of the tubular portion 43a of the frame 43.

Next, a mechanism for bending the coil assembly 30 will now be described. This mechanism comprises two operating wires 51 and 52. The operating wires 51 and 52 are fixedly secured at their one ends to an outer peripheral surface of a pulley 50 mounted within the body 1, and the operating wires 51 and 52 extend forwardly respectively from upper and lower sides of the pulley 50. The pulley 50 is connected to the manipulating dial 13 via a shaft (not shown) extending through the wall of the body 1.

At the insertion portion 2, the operating wires 51 and 52 are passed respectively through a pair of guide coils 53 and 54 of a small diameter. The upper and lower guide coils 53 and 54 are mounted within the holder coil 28, and are circumferentially spaced 180° from each other in opposed relation to each other. The proximal ends of the guide coils 53 and 54 are fixedly secured to the body 1, and the distal ends thereof are fixedly secured to the inner peripheral surface of the connecting tube 29.

At the bending portion 3, the operating wires 51 and 52 extend respectively through the spaces S1 and S2 formed by the coils 31 and 32, and the distal ends of these operating wires are fixedly secured to the frame 43 of the rigid portion 4 by brazing or the like.

The central portions of the spaces S1 and S2 formed by the coils 31 and 32 are disposed in opposed relation to the guide coils 53 and 54, respectively With this arrangement, the operating wires 51 and 52 can extend straight.

The endoscope includes a flexible, resilient resin tube 60 made of a plastics material, rubber or the like. The resin tube 60 covers the insertion portion 2, the bending portion 3 and the rigid portion 4. The holder coil 28 and the connecting tube 29 of the insertion portion 2, the coil assembly 30 of the bending portion 3, and the frame 43 of the rigid portion 4 are embedded in the peripheral wall of the resin tube 60. The axis of the resin tube 60 are in alignment with the axes of the holder coil 28, the connecting tube 29, the tubular portion 43a of the frame 43, and the center line 0 of the coil assembly 30. The guide coils 53 and 54 as well as the operating wires 51 and 52 are embedded respectively in the upper and lower portions of the peripheral wall of the resin tube 60. The resin tube 60 may be provided only at the bending portion 3.

An internal space S' of a circular cross-section is defined by the inner peripheral surface of the resin tube 60. Of course, the internal space S' is smaller in cross-section than the space S formed by the inner peripheries of the coils 31 and 32. The optical fiber bundle for transmitting the image, the optical fiber bundle for transmitting the illumination light, the guide tube for guiding the forceps, and etc., are passed through the internal space S'. An end wall 60a is formed at the distal end of the resin tube 60, and the inspection window 41 and the illumination window 42 disposed in registry respectively with the holes 43x and 43y in the frame 43 are formed through the end wall 60a.

In the case where the resin tube 60 is used as in this embodiment, the use of the guide coils 53 and 54 may be omitted.

In the above construction, when the manipulating dial 13 is rotated in a clockwise direction (FIG. 1), the operating wire 51 is pulled whereas the operating wire 52 is loosened. As a result, the bending portion 3 is bent upward. At this time, the length of the coil assembly 30 is not changed in the plane including the contact points X and X', and the upper portion of the coil assembly 30 is contracted whereas the lower portion thereof is expanded. In contrast, when the manipulating dial 13 is rotated in a counterclockwise direction, the operating wire 52 is pulled whereas the operating wire 51 is loosened. As a result, the bending portion 3 is bent downward At this time, the upper portion of the coil assembly 30 is expanded whereas the lower portion thereof is contracted The resin tube 60 also performs the function of resiliently supporting the coil assembly 30. Therefore, the spaced-apart relation between the axes L1 and L2 of the coils 31 and 32 can be maintained.

In the bending portion 3 of the above construction for the endoscope, the coil assembly 30 composed of the two coils 31 and 32 provides the flexibility of the bending portion 3, and also serves to guide the operating wires 51 and 52. The construction of the bending portion 3 is very simple, and therefore the manufacturing cost thereof can be reduced greatly.

Since there is no projection, such as a guide member for the operating wires, in the internal space S' of the resin tube 60, there is no possibility that the optical fiber bundles may be damaged by such projection.

Next, modified bending portions of the present invention will be described below with reference to FIGS. 4 to 20. Those portions of these embodiments corresponding to those of the preceding embodiment are denoted by identical reference numerals, respectively, and detailed explanation thereof will be omitted here.

Figure 4:
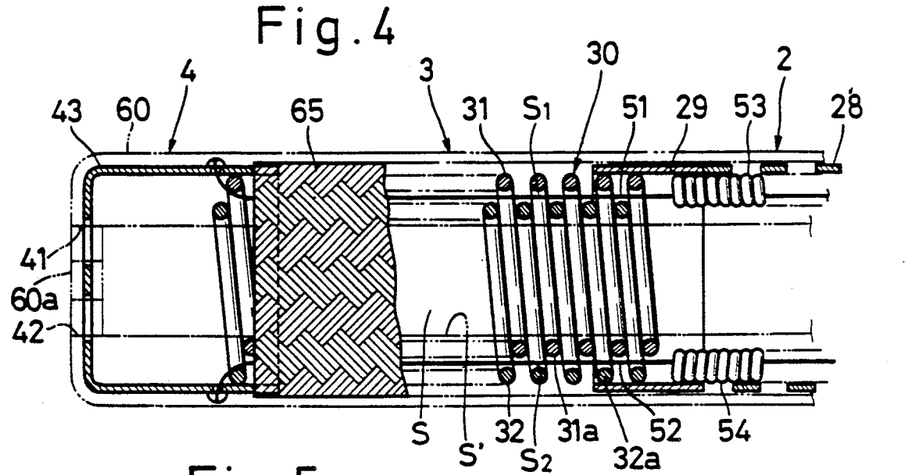
FIGS. 4 and 5 are views similar to FIG. 2, but showing modified bending portions, respectively.

In the embodiment shown in FIG. 4, a braid tube 65 is disposed around a holder coil 28, a connecting tube 29 and a coil assembly 30. The braid tube 65 is made of a conventional braid composed of thin metal yarns, resin fibers, or the like The proximal end of the braid tube 65 is fixedly secured to a body 1, and the distal end thereof is fixedly secured to a frame 43 of a rigid portion 4. The braid tube 65 is embedded in a peripheral wall of a resin tube 60.

Figure 5:
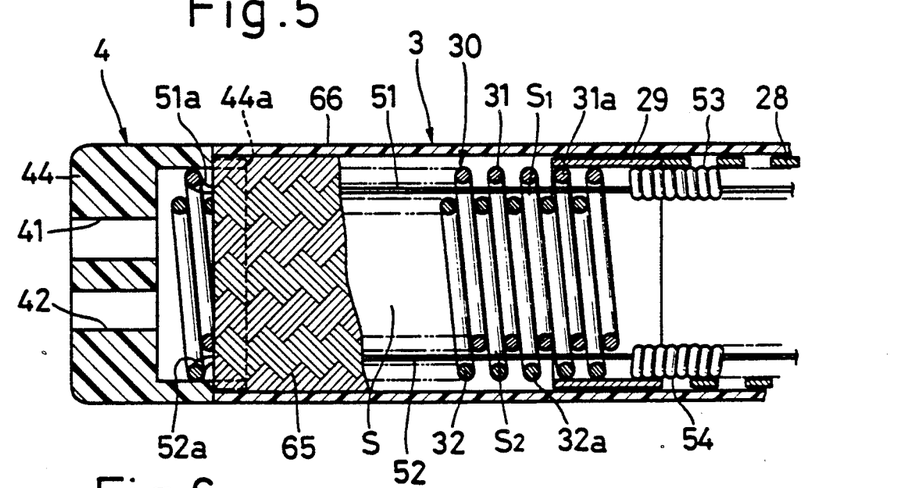
Figure 6:
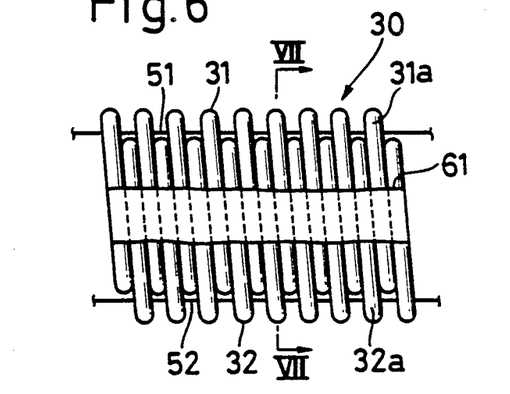
FIG. 6 is a side-elevational view of the bending portion of FIG. 5.
Figure 7:
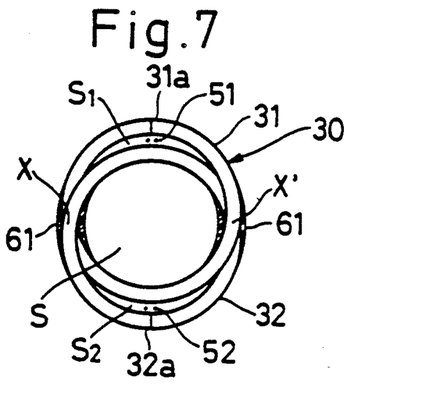
FIG. 7 is a cross-sectional view taken along the line VII—VII of FIG. 6.

The embodiment shown in FIGS. 5 to 7 is similar to the embodiment of FIG. 4 in that it is provided with a braid tube 65, but the resin tube 60 of FIG. 4 is not used in this embodiment. Therefore, at a bending portion 3, the optical fiber bundles are passed through an internal space S formed by the inner peripheries of coils 31 and 32. An outer sheath 66 made of a heat-shrinkable resin is provided around the braid tube 65. In this embodiment, two resilient support members 61 and 61 are attached to a coil assembly 30, and extend along the axis of the coil assembly. One of the two resilient support members 61 and 61 extends along and embraces a series of points X of contact between the two coils 31 and 32, and the other resilient support member 61 extends along and embraces a series of points X' of contact between the two coils 31 and 32. Each resilient support member 61 is made of a flexible, resilient resin adhesive. Because of the provision of the two resilient support members 61 and 61, the radially spaced-apart relation between the axes of the two coils 31 and 32 is maintained. In this embodiment, a rigid portion 4 comprises a rigid resin member 44 having a tubular portion 44a at its rear end portion, and the distal end of the braid tube 65 is fitted on and fixedly secured to the outer peripheral surface of the tubular portion 44a. Each of operating wires 51 and 52 is constituted by a single wire folded in two, and folded portions 51a and 51b of these wires are engaged with the distal ends of the two coils 31 and 32, respectively. Thus, the operating wires 51 and 52 are substantially fixed relative to the two coils 31 and 32, respectively.

Figure 8:
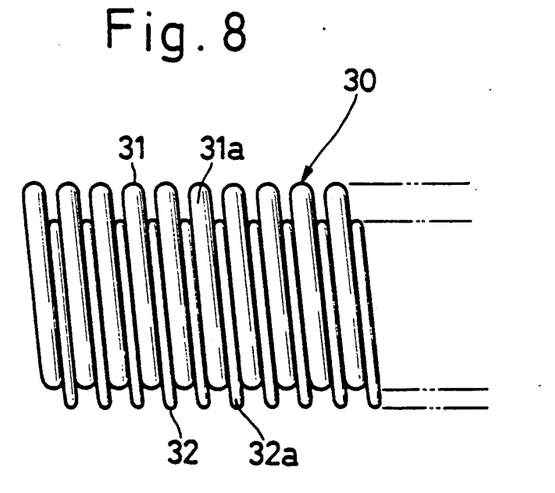
FIG. 8 is a view similar to FIG. 6, but showing a further modified bending portion.

In the embodiment shown in FIG. 8, although two coils 31 and 32 are equal in diameter to each other the diameter (thickness) of a wire 31a constituting the coil 31 is greater than the diameter (thickness) of a wire 32a constituting the coil 32.

Figure 9:
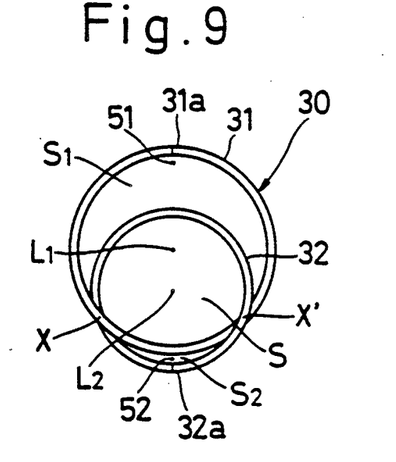
FIGS. 9 to 11 are views similar to FIG. 3, but showing further modified bending portions, respectively.

In the embodiment shown in FIG. 9, a coil 31 is greater in diameter than a coil 32. In this embodiment, the distance between one operating wire 51 and a plane in which contact points X and X' lie is greater than the distance between the other operating wire 52 and this plane. Therefore, a moment produced when bending a bending portion 30 by pulling the operating wire 51 is greater than a moment produced when bending the bending portion 30 by pulling the operating wire 52. This construction is advantageous in the case where component parts received within an internal space S have different bending resistances. More specifically, in such a case, those component parts having greater bending resistances are disposed in that side of the internal space S close to the operating wire 52 whereas those component parts having less bending resistances are disposed in that side of the internal space S close to the operating wire 51. With this arrangement, the force required for an upward bending of the bending portion 3 can be made equal to the force required for a downward bending of the bending portion 3.

Figure 10:
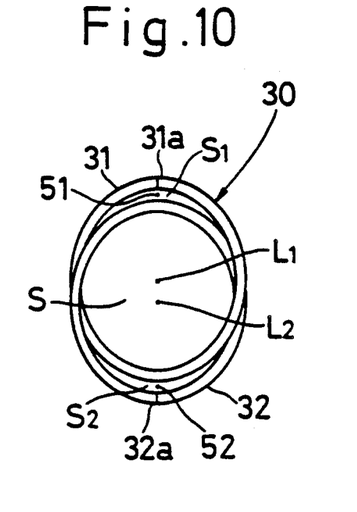

In the embodiment shown in FIG. 10, two coils 31 and 32 are of an identical shape, each turn of each of the two coils 31 and 32 has an oval shape as viewed in an axial direction thereof. The long axes of the ovals of the turns of the coils 31 and 32 coincide with each other as viewed in the direction of the axis of a coil assembly 30, that is, are disposed in a common plane. Axes L1 and L2 of the coils 31 and 32 are spaced from each other along the long axes of the ovals of the turns of the coils 31 and 32.

Figure 11:
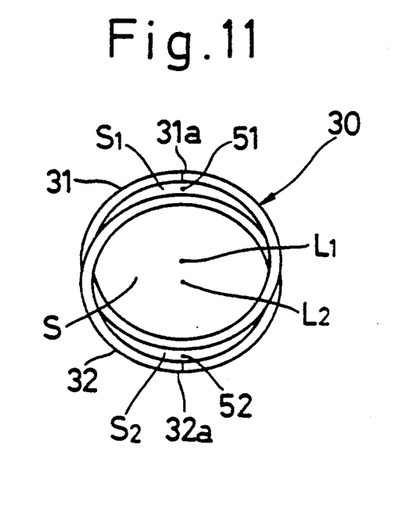

In the embodiment shown in FIG. 11, as in the embodiment of FIG. 10, each turn of each of two coils 31 and 32 has an oval shape as viewed in an axial direction thereof, but in this embodiment the short axes of the ovals of the turns of the coils 31 and 32 coincide with each other as viewed in the direction of the axis of a coil assembly 30, that is, are disposed in a common plane. Axes L1 and L2 of the coils 31 and 32 are spaced from each other along the short axes of the ovals of the turns of the coils 31 and 32.

Figure 12:
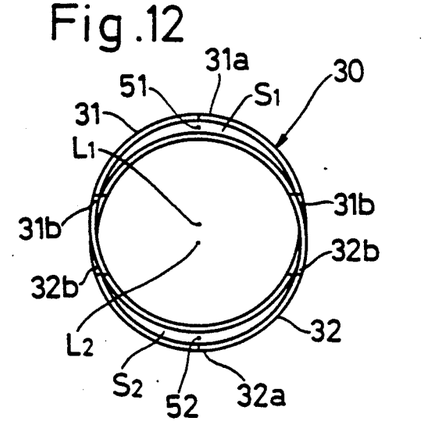
FIG. 12 is a view similar to FIG. 3, but showing a further modified bending portion.
Figure 13:
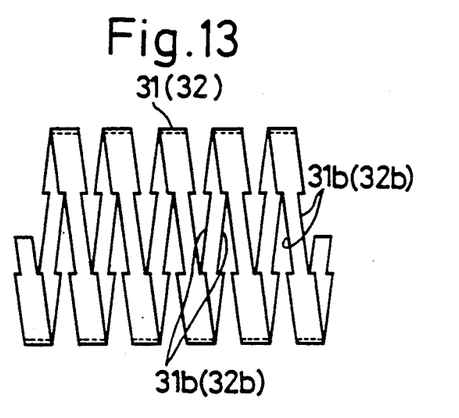
FIG. 13 is a side-elevational view of one coil of the bending portion of FIG. 12.

In the embodiment shown in FIGS. 12 and 13, two coils 31 and 32 are made of strip-like plates 31a and 32a respectively. A pair of notches 31b (32b) are formed respectively in opposite side edges of each turn of each of the coils 31 and 32 at each of diametrically-opposite two portions of the turn (i.e., two portions circumferentially spaced 180° from each other). When the coils 31 and 32 are in an assembled condition the recessed edges of the notches 31b and 32b of any two adjacent turns of the coils 31 and 32 are held in contact with each other. FIG. 13 shows an axially expanded condition of the coil 31 (32).

Figure 14:
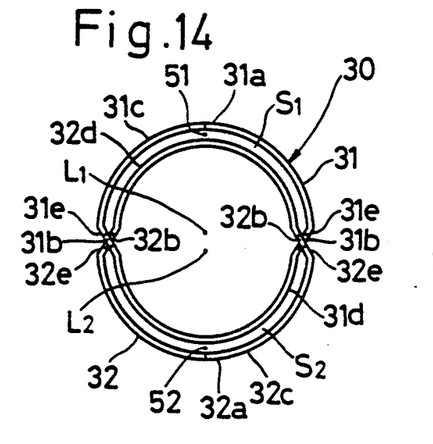
FIG. 14 is a view similar to FIG. 3, but showing a further modified bending portion.
Figure 15:
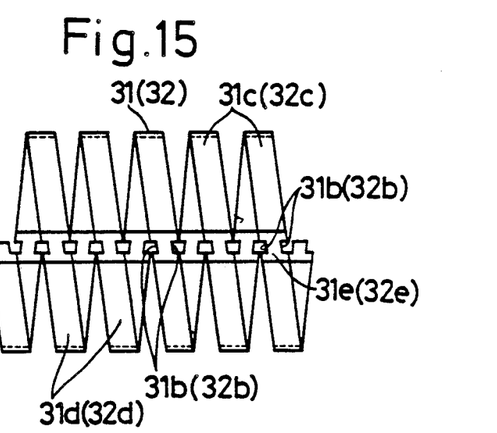
FIG. 15 is a side-elevational view of one coil of the bending portion of FIG. 14.

The embodiment shown in FIGS. 14 and 15 is similar to the embodiment of FIGS. 12 and 13 in that two coils 31 and 32 are made of strip-like plates 31a and 32a, respectively, and that a pair of notches 31b (32b) are formed respectively in each turn of each of the coils 31 and 32. However, this embodiment differs from the embodiment of FIGS. 12 and 13 in the following respects. Each turn of the coil 31 has a greater semi-circular portion 31c, a smaller semi-circular portion 31d, and a pair of substantially flat connecting portions 31e interconnecting the two semi-circular portions 31c and 31d at their opposite ends. The greater semi-circular portion 31c as well as the smaller semi-circular portion 31d is generally in the shape of a half of a circle. The notches 31b are formed respectively in the opposite side edges of each connecting portion 31e. Similarly, each turn of the coil 32 has a greater semi-circular portion 32c, a smaller semi-circular portion 32d, and a pair of substantially flat connecting portions 32e interconnecting the two semi-circular portions 32c and 32d at their opposite ends. The greater semi-circular portion 32c as well as the smaller semi-circular portion 32d is generally in the shape of a half of a circle. The notches 32b are formed respectively in the opposite edges of each connecting portion 32e.

In the embodiment of FIGS. 14 and 15, the flat connecting portions 31e and 32e of any two adjacent turns of the coils 31 and 32 intersect each other at a relatively large angle. Therefore, the width of the notch 31 (32b) can be reduced in the circumferential direction of the coil 31 (32). The engagement between the notches 31b and 32b maintains a spacedapart relation between axes L1 and L2 of the coils 31 and 32.

In all of the above embodiments, although two series of points of contact between the coils 31 and 32 are disposed respectively in two straight lines parallel to the axes of the coils 31 and 32, each of these two series of contact points may be disposed along a spiral line. To achieve this, the two coils 31 and 32 are combined together in such a manner that the above two series of contact points are disposed respectively in the two straight lines, as in the above embodiments. Then, one ends of the coils 31 and 32 are fixed against movement, and the other ends thereof are twisted in the same direction in the same amount, so that the two series of contact points are disposed in spiral lines, respectively. In this case, the above-mentioned resin tube 60, etc., serve to maintain this twisted condition. In this case, each of the operating wires 51 and 52 is also spiral, and when one of the two operating wires 51 and 52 is pulled, the bending portion 3 is bent spirally. In this case, a spiral motion of the bending portion 3 effected by pulling one operating wire 51 occurs in a direction reverse to the direction of a spiral motion of the bending portion 3 effected by pulling the other operating wire 52.

In each of the above embodiments, although the coil assembly 30 has the two coils 31 and 32, the coil assembly may have three or more coils as described below.

Figure 16:
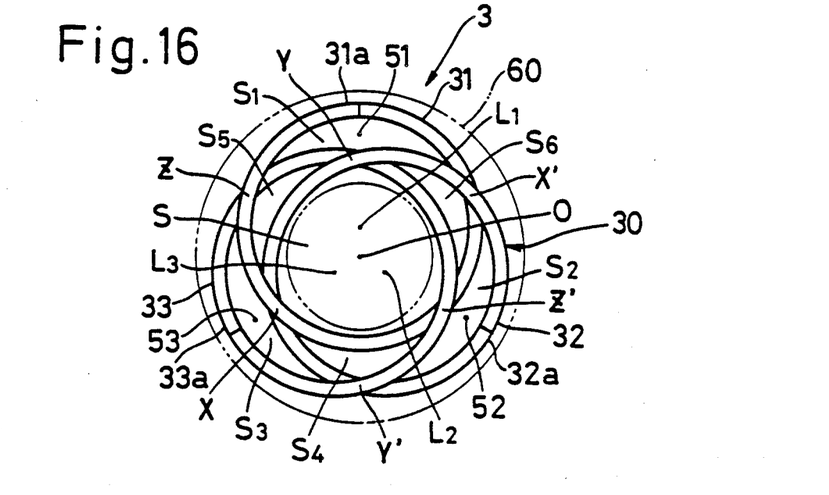
FIG. 16 is a view similar to FIG. 3, but showing a further modified bending portion.

In the embodiment shown in FIG. 16, a coil assembly 30 comprises three coils 31, 32 and 33. Axes L1, L2 and L3 of the coils 31, 32 and 33 are parallel to one another, and are spaced equidistantly from a center line 0 of the coil assembly 30, and are circumferentially spaced at an equal interval from one another around the center line 0. In other words, the axes L1, L2 and L3 are disposed respectively at apexes of a regular or equilateral triangle. The turns of the coils 31, 32 and 33 alternate with one another along the axis of the coil assembly 30. Any two adjacent turns of the coils 31, 32 and 33 are held in contact with each other at two points. More specifically, the two points of contact between the adjacent turns of the coils 31 and 32 are denoted respectively by X and X' in FIG. 16, and the two points of contact between the adjacent turns of the coils 32 and 33 are denoted respectively by Y and Y', and the two points of contact between the adjacent turns of the coils 33 and 31 are denoted respectively by Z and Z'. With this arrangement of the three coils 31, 32 and 33, a space S1 is formed between the inner periphery of the coil 31 and the outer peripheries of the coils 32 and 33. Similarly, a space S2 is formed between the inner periphery of the coil 32 and the outer peripheries of the coils 31 and 33, and a space S3 is formed between the inner periphery of the coil 33 and the outer peripheries of the coils 31 and 32. The three spaces S1, S2 and S3 extend along the axis of the coil assembly 30. Operating wires 51, 52 and 53 extend through the spaces S1, S2 and S3, respectively.

In the embodiment of FIG. 16, the bending portion 3 can be bent in any one of six different directions by pulling the operating wire 51, or pulling the operating wire 52, or pulling the operating wire 53, or simultaneously pulling the two operating wires 52 and 53, or simultaneously pulling the two operating wires 51 and 53, or simultaneously pulling the two operating wires 51 and 52.

A space S4, S5, S6 is also formed between the outer periphery of one of the three coils 31, 32 and 33 and the inner peripheries of the other two. The operating wires 51, 52 and 53 may be passed through these spaces S4, S5 and S6, respectively.

Figure 17:
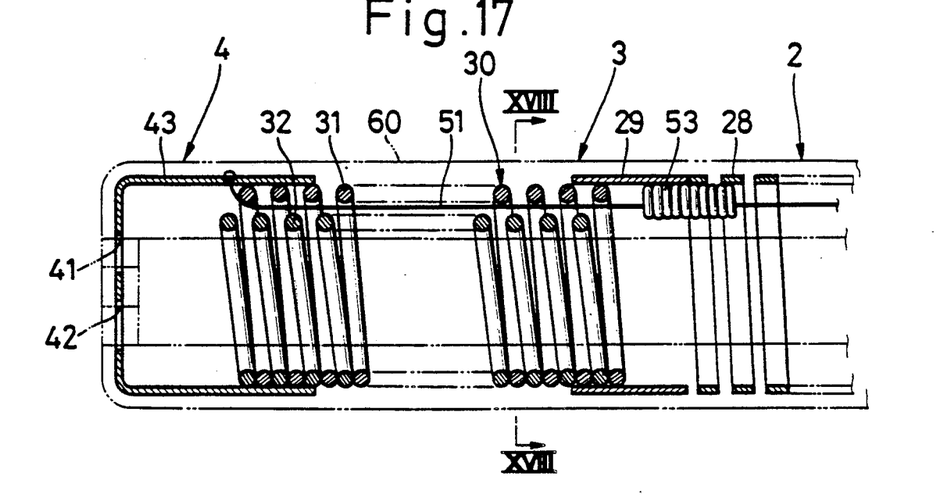
FIG. 17 is a view similar to FIG. 2, but showing a further modified bending portion.
Figure 18:
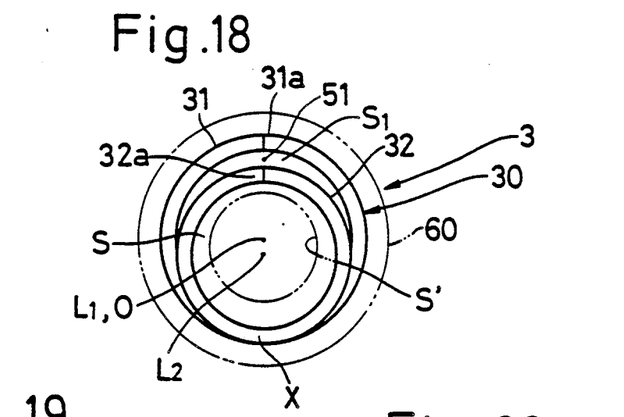
FIG. 18 is a cross-sectional view taken along the line XVIII—XVIII of FIG. 17.

FIGS. 17 and 18 shows a further modified bending portion which can be bent only in one direction. A coil assembly 30 of the bending portion 3 of this embodiment comprises a greater-diameter coil 31 and a smaller-diameter coil 32, each turn of each of the coils 31 and 32 being circular as viewed in the direction of the axis of the coil. The coils 31 and 32 are composed respectively of wires 31a and 32a having the same circular cross-section. An axis L1 of the greater-diameter coil 31 is disposed in alignment with a center line 0 of the bending portion 3. An axis L2 of the smaller-diameter coil 32 is radially spaced from the axis L1 of the greater-diameter coil 31. The turns of the two coils 31 and 32 alternate with each other, and any two adjacent turns of the coils 31 and 32 are held in contact with each other only at one point X. The outer periphery of the smaller-diameter coil 32 is disposed inwardly of the outer periphery of the greater-diameter coil 31 except at a region corresponding to the contact point X. As a result, one side portion (lower portion) of the coil assembly 30 is unable to be contracted axially, and the other side portion (upper portion) of the coil assembly 30 can be contracted axially. An upper space S1 is formed between the inner periphery of the greater-diameter coil 31 and the outer periphery of the smaller-diameter coil 32. An operating wire 51 is passed through the space S1. An internal space S of the coil assembly 30 is defined by the inner periphery of the smaller-diameter coil 32.

In the embodiment of FIGS. 17 and 18, when the operating wire 51 is pulled, the upper portion of the coil assembly 30 is axially contracted, so that the bending portion 3 is bent upward. When the pulling force thus applied to the operating wire 51 is released, the bending portion 3 is restored or returned into a straight condition because of the resilient natures of the coil assembly 30 and a resin tube 60.

Figures 19, 20:
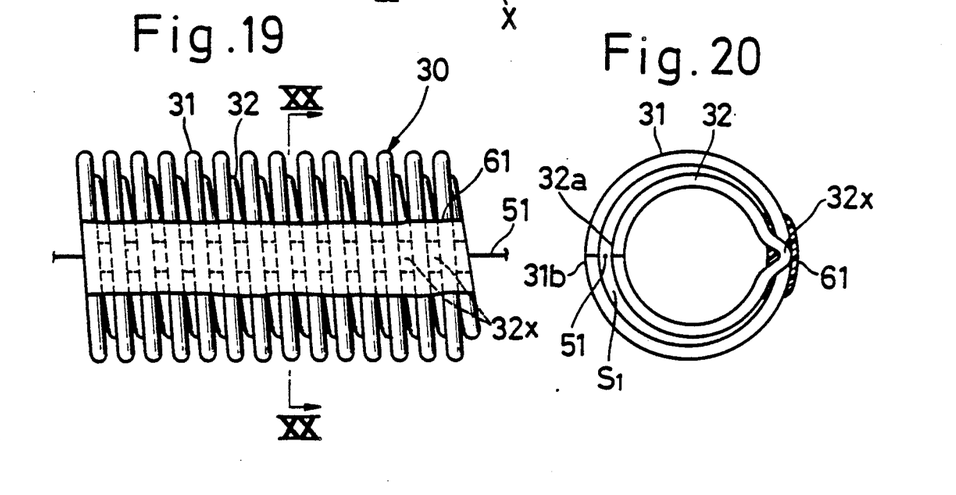
FIG. 19 is a side-elevational view of a further modified bending portion.
FIG. 20 is a cross-sectional view taken along the line XX—XX of FIG. 19.

In the embodiment shown in FIGS. 19 and 20, a radially outwardly-directed projection 32x is formed on each turn of a smaller-diameter coil 32. Each projection 32x is fitted in a space between two adjacent turns of a greater-diameter coil 31. The remainder of the smaller-diameter coil 32 other than the projection 32x is disposed inwardly of the inner periphery of the greater-diameter coil 31. A resilient support member 61 extends along the axis of a coil assembly 30, and embraces a series of points X of contact between the projections 32x and the respective turns of the greater-diameter coil 31, thereby supporting those portions of the coils 31 and 32 disposed in contact with each other. The resilient support member 61 is made of a flexible, resilient resin adhesive, as in the embodiment of FIG. 7.

In the embodiment of FIGS. 19 and 20, the area of contact between the greater-diameter coil 31 and the smaller-diameter coil 32 can be made considerably small, thus providing the point-to-point contact between the adjacent turns of the coils 31 and 32 in a strict sense.

Even in the coil assemblies of the type in which the adjacent turns of the two coils are in contact with each other only at one point, the turns of the two coils may be oval, and the thicknesses of the two coils are different from each other, as described above for the coil assemblies in which the turns of the two coils are in contact with each other at two points.

The bending portions 3 in all of the above embodiments can also be recognized as flexible tube structures of the present invention.

Figure 21:
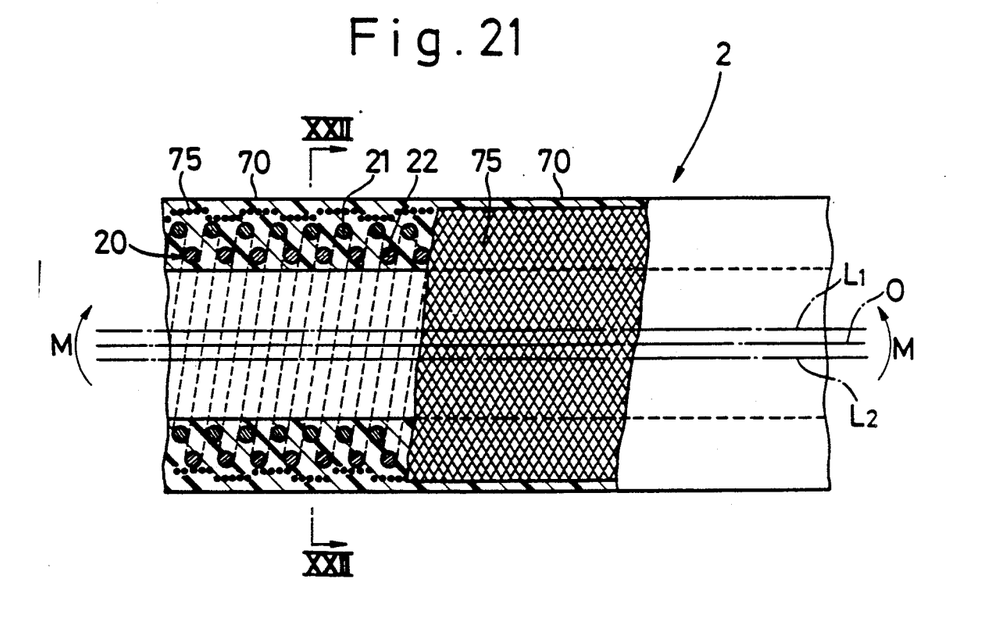
FIG. 21 is a cross-sectional view of an insertion portion of an endoscope.
Figure 22:
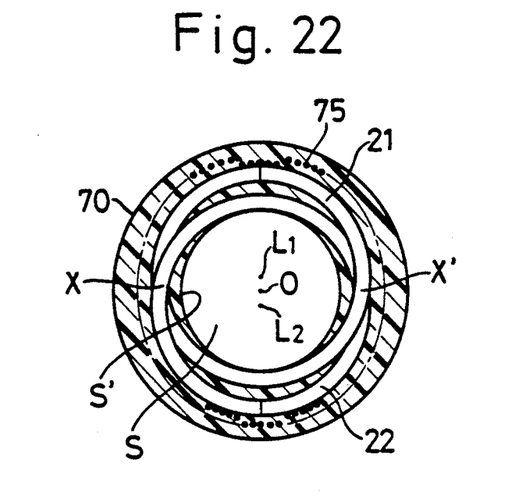
FIG. 22 is a cross-sectional view taken along the line XXII—XXII of FIG. 21.

Next, one example of a flexible tube structure of the present invention applied to an insertion portion of an endoscope will now be described with reference to FIGS. 21 to 23. The type of endoscope to which the flexible tube structure of this embodiment is applied is not provided with a bending portion, and has a rigid portion mounted on the distal end of the insertion portion. The insertion portion 2 shown in FIG. 21 comprises a coil assembly 20 composed of two coils 21 and 22 of an identical shape. The coil assembly 20 is similar in construction to the coil assemblies 30 of the bending portions 3 described in the above embodiments, and therefore detailed explanation thereof will be omitted here. In the drawings, reference characters L1 and L2 denote the axes of the coils 21 and 22, respectively, and reference character 0 denotes the center line of the coil assembly 20, and reference character S denotes an internal space formed by the inner peripheries of the coils 21 and 22.

A braid tube 75 of a cylindrical shape is disposed around the two coils 21 and 22, and is in contact therewith. The coil assembly 20 and the braid tube 75 are embedded in a peripheral wall of a resilient resin tube 70. The resin tube 75 has an internal space S' defined by the inner periphery thereof. Optical fiber bundles, etc., are received in the internal space S'.

In the insertion portion 2 of the above construction, the resin tube 70 and the braid tube 75 are flexible. It will be readily understood that when the coil assembly 20 is subjected to a bending moment acting in a direction M (FIG. 21) or a bending moment acting in a direction opposite to the direction M, the coil assembly 20 can be bent, with points X and X' of contact between the coils 21 and 22 serving as fulcrums. When the coil assembly 20 is subjected to a bending moment acting in a direction perpendicular to the direction M, the coil assembly 20 can be bent on condition that the center axis 0 of the insertion portion 2 can be expanded or elongated. The expansion of the center axis 0 means the axial expansion of the braid tube 75, and therefore this expansion requires the reduction of the diameter of the braid tube 75. This can be achieved by a slight radially-inward movement of the two coils 21 and 22 toward each other. In the case where part of the material of the resilient resin tube 70 exists between the braid tube 75 and the coil assembly 20, the reduction of the diameter of the braid tube 75 can also be achieved by the resiliency of said part of the material.

Therefore, when the insertion portion 2 is to be inserted into the trachea or the blood vessel, the insertion portion 2, because of its flexibility, can be smoothly inserted thereinto without receiving a resistance.

Further, since any two adjacent turns of the two coils 21 and 22 of the coil assembly are held in contact with each other, the insertion portion 2 will not be compressed axially. Therefore, the insertion of the insertion portion 2 particularly into the trachea or the blood vessel can be done more smoothly.

In the insertion portion 2, the braid tube 75 is disposed around the coil assembly 20, and therefore when a pulling force is applied to the insertion portion 2, the insertion portion 2 can be prevented from being unduly expanded axially.

Figure 23:
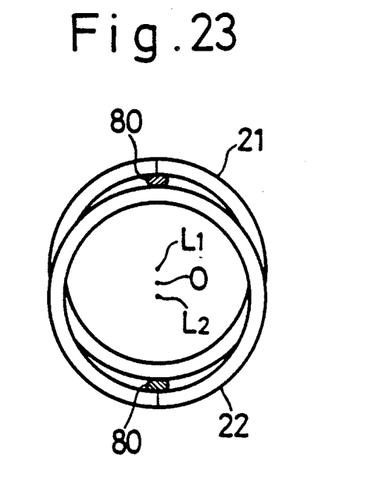
FIG. 23 is a cross-sectional view showing a process of manufacturing the insertion portion of the endoscope.
Figure 24:
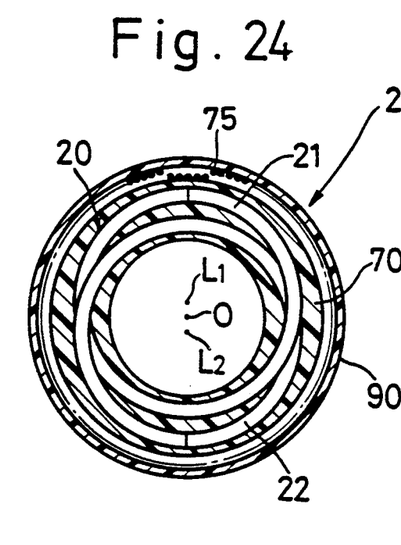
FIGS. 24 to 26 are views similar to FIG. 22, but showing modified insertion portions, respectively.

For manufacturing the flexible tube structure constituting the insertion portion 2, first, the two coils 21 and 22 are combined together as shown in FIG. 23, and a pair of bar-like spacers 80 and 80 are inserted respectively into two spaces formed respectively between the inner periphery of the coil 21 and the outer periphery of the coil 22 and between the outer periphery of the coil 21 and the inner periphery of the coil 22, thereby maintaining a predetermined positional relation between the two coils 21 and 22. Then, the braid tube 75 is fitted on the combined coils 21 and 22 and is disposed in intimate contact with the outer peripheries of the coils 21 and 22. Thereafter, the resin tube 70 is molded in such a manner that the coils 21 and 22 and the braid tube 75 are embedded in the periphery wall of the resin tube 70. The spacers 80 and 80 may be inserted respectively into the coils 21 and 22 before the coils 21 and 22 are combined together, In the case where the spacers 80 are resilient, these spacers may be allowed to remain as part of the insertion portion 2. However, in the case where the spacers 80 have a relatively high bending resistance, the spacers 80 are removed or withdrawn from the molded resin tube 70. Holes, formed in the resin tube 70 as a result of the removal of the spacers 80, may remain intact or be filled with a suitable material In a modified flexible tube structure shown in FIG. 24, a coil assembly 20 is embedded in a peripheral wall of a resilient resin tube 70. A braid tube 75 is fitted on the resin tube 70, and an outer sheath 90 made of a resilient resin is fitted on the braid tube 75.

Figure 25:
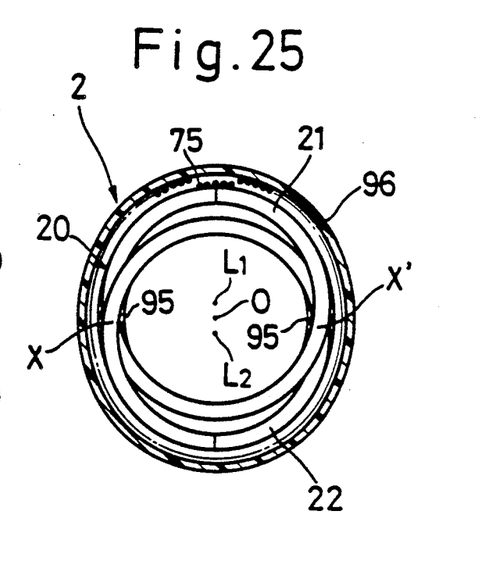

In another modified flexible tube structure shown in FIG. 25, an insertion portion 2 has two resilient support members 95 and 95 extending along the axis of the insertion portion 2. One of the two resilient support members 95 and 95 extends along and embraces a series of points X of contact between the two coils 21 and 22, and the other resilient support member 95 extends along and embraces a series of points X' of contact between the two coils 21 and 22. Thus, the two resilient support members 95 and 95 resiliently support those portions of the two coils 21 and 22 disposed in contact with each other. A braid tube 75 is fitted on a coil assembly 20, and an outer sheath 96 in the form of a heat-shrinkable tube is fitted on the braid tube 75.

Figure 26:
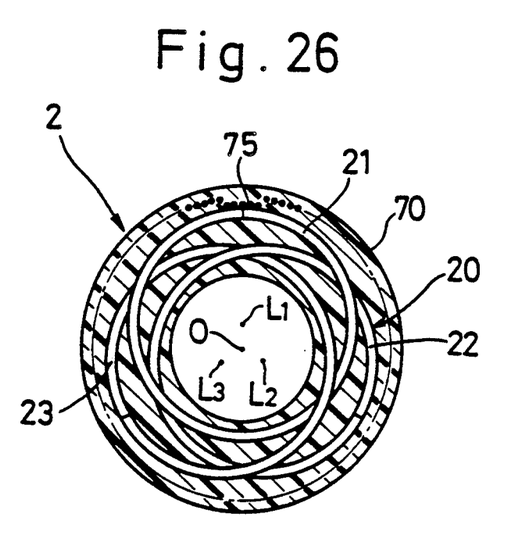

In a further modified flexible tube structure shown in FIG. 26, a coil assembly 20 comprises three coils 21, 22 and 23. This coil assembly 20 is similar in construction to the coil assembly 30 of FIG. 16, and therefore detailed explanation of the coil assembly 20 will be omitted here, Also, the coil assemblies 30 shown in FIGS. 8 to 15 and 17 to 20 can also be used as the coil assembly of the insertion portion.

The bending devices according to the present invention can be used in a medical catheter The flexible tube structures according to the present invention can be applied to an insertion portion or a bending portion of a catheter, and also can be applied to a guide tube for guiding a forceps in an endoscope.

What is claimed is:

1. A bending device comprising:
   (a) operating wire means adapted to be pulled at a proximal end of said bending device; and
   (b) a coil assembly comprising a plurality of coils which are combined together in such a manner that turns of said plurality of coils alternate with each other, any two adjacent turns of said plurality of coils being disposed in substantially point-to-point contact relation to each other, a space extending axially' of said coils and being formed between peripheries of said plurality of coils, said operating wire being passed through said space means, and a distal end of said operating wire means being substantially fixed relative to a distal end of said coil assembly.

2. A bending device according to claim 1, further comprising resilient support means resiliently supporting those portions of said plurality of coils disposed in contact with each other.

3. A bending device according to claim 1, in which axes of said plurality of coils are substantially parallel to each other and are spaced from each other radially of said coils, any two adjacent turns of said plurality of coils being held in contact with each other at two points.

4. A bending device according to claim 3, in which said operating wire means comprises a first and a second operating wire, said coil assembly comprising a first coil and a second coil which constitute said plurality of coils, said space comprising a first space formed between an inner periphery of said first coil and an outer periphery of said second coil, and a second space formed between an outer periphery of said first coil and an inner periphery of said second coil, and said first and second operating wires being passed respectively through said first and second spaces.

5. A bending device according to claim 4, in which each of said first and second coils is made of a strip-like plate, a pair of notched portions being formed respectively in opposite side edges of each of generally diametrically-opposite two portions of each turn of each of said first and second coils, each of said notched portions having a recessed edge, and said recessed edges of any two adjacent turns of said first and second coils being disposed in contact with each other.

6. A bending device according to claim 3, in which said coil assembly comprises three said coils, axes of said three coils being disposed respectively at apexes of a triangle, said space means comprises three spaces spaced from one another circumferentially of said coil assembly, and said operating wire means comprising three operating wires which are passed respectively through said three spaces.

7. A bending device according to claim 1, in which said coil assembly comprises two said coils, one of which has a greater diameter than the other, said coil of a smaller diameter being disposed inwardly of an outer periphery of said coil of a greater diameter in such a manner that any two adjacent turns of said two coils are disposed in contact with each other substantially at one point, said space comprising one space formed between an outer periphery of said smaller-diameter coil and an inner periphery of said greater-diameter coil, said operating wire means comprising a single operating wire, and said operating wire being passed through said space.

8. A bending device according to claim 7, in which each turn of each of said two coils has a substantially circular shape, each turn of said smaller-diameter coil having a projection extending radially outwardly, said projection being fitted in a space between any two adjacent turns of said greater-diameter coil, and said operating wire being disposed remote from said projection.

9. A flexible tube structure comprising:
 (a) flexible outer tube means; and
 (b) a coil assembly mounted within said outer tube means, said coil assembly comprising a plurality of coils which are combined together in such a manner that turns of said plurality of coils alternate with each other, any two adjacent turns of said plurality of coils being disposed in substantially point-to-point contact relation to each other, an internal space being formed by an inner periphery of at least one of said plurality of coils.

10. A flexible tube structure according to claim 9, further comprising a resilient resin tube, said coil assembly being embedded in a peripheral wall of said resilient resin tube, and those portions of said resilient resin tube which embrace those portions of said plurality of coils disposed in contact with each other serving as support means supporting said coils.

11. A flexible tube structure according to claim 9, further comprising at least one resilient support member extending along the axis of said coil assembly, said resilient support member embracing those portions of said plurality of coils disposed in contact with each other.

12. A flexible tube structure according to claim 9, in which said coil assembly comprises a first coil and a second coil which constitute said plurality of coils, axes of said two coils being substantially parallel to each other and being spaced from each other radially of said coils, and part of one of said two coils projecting radially outwardly from an outer periphery of the other coil, so that said internal space is formed by inner peripheries of said two coils.

13. A flexible tube structure according to claim 9, in which said coil assembly comprises two said coils one of which has a greater diameter than the other, said coil of a smaller diameter being disposed inwardly of an outer periphery of said coil of a greater diameter in such a manner that any two adjacent turns of said two coils are disposed in contact with each other substantially at one point, and said internal space being formed by an inner periphery of said smaller-diameter coil.

14. A flexible tube structure according to claim 9, in which said coil assembly comprises three said coils, axes of said three coils being disposed respectively at apexes of a triangle, and said internal space being formed by inner peripheries of said three coils.

* * * * *